United States Patent [19]

Hotchkiss et al.

[11] Patent Number: 5,372,597
[45] Date of Patent: Dec. 13, 1994

[54] SUPINATION-PRONATION DEVICE

[75] Inventors: Robert N. Hotchkiss, Riverside, Conn.; John Popken, Longmont; Arthur Woodward, Lakewood, both of Colo.; Mark S. Gosney, Memphis, Tenn.

[73] Assignee: Smith & Nephew Richards, Inc., Memphis, Tenn.

[21] Appl. No.: 60,855

[22] Filed: May 12, 1993

[51] Int. Cl.$^5$ .................................. A61F 5/00
[52] U.S. Cl. .................................. 606/56; 606/54; 606/57; 606/105; 602/20
[58] Field of Search .................. 606/54–59, 606/105; 602/6, 20–21

[56] References Cited

U.S. PATENT DOCUMENTS

| | | | |
|---|---|---|---|
| 2,391,537 | 12/1945 | Anderson | 606/59 |
| 3,709,219 | 1/1973 | Hallorah | 606/57 X |
| 3,976,061 | 8/1976 | Volkov et al. | 606/56 |
| 3,977,397 | 8/1976 | Kalnberz et al. | 606/57 |
| 4,100,919 | 7/1978 | Oganesyan et al. | 606/56 |
| 4,535,763 | 8/1985 | Jaquet | 606/59 X |
| 4,768,524 | 9/1988 | Hardy | 606/54 |
| 4,848,326 | 7/1989 | Lonardo . | |
| 4,923,458 | 5/1990 | Fischer | 606/59 |
| 5,087,258 | 2/1992 | Schewior | 606/59 X |
| 5,100,403 | 3/1992 | Hotchkiss . | |
| 5,102,411 | 4/1992 | Hotchkiss . | |
| 5,117,814 | 6/1992 | Luttrell et al. . | |
| 5,167,612 | 12/1992 | Bonutti . | |

FOREIGN PATENT DOCUMENTS

| | | | |
|---|---|---|---|
| 1481585 | 8/1977 | United Kingdom | 606/56 |
| 1149952 | 4/1985 | U.S.S.R. | 606/56 |
| 1161101 | 6/1985 | U.S.S.R. | 606/57 |

Primary Examiner—Richard J. Apley
Assistant Examiner—Linda C. M. Dvorak
Attorney, Agent, or Firm—Pravel, Hewitt, Kimball & Krieger

[57] ABSTRACT

A device for treating and preventing injuries and contractures of the elbow joint, particularly supination-pronation contractures and proximal radial head fractures. The device includes bracing sections for fixing the device to the radius and the ulna, and for permitting movement of the attached radius continually along a path which is adapted and adjusted to be aligned with the kinematic axis of the proximal radial-ulnar joint.

13 Claims, 4 Drawing Sheets

FIG. 4
FIG. 5
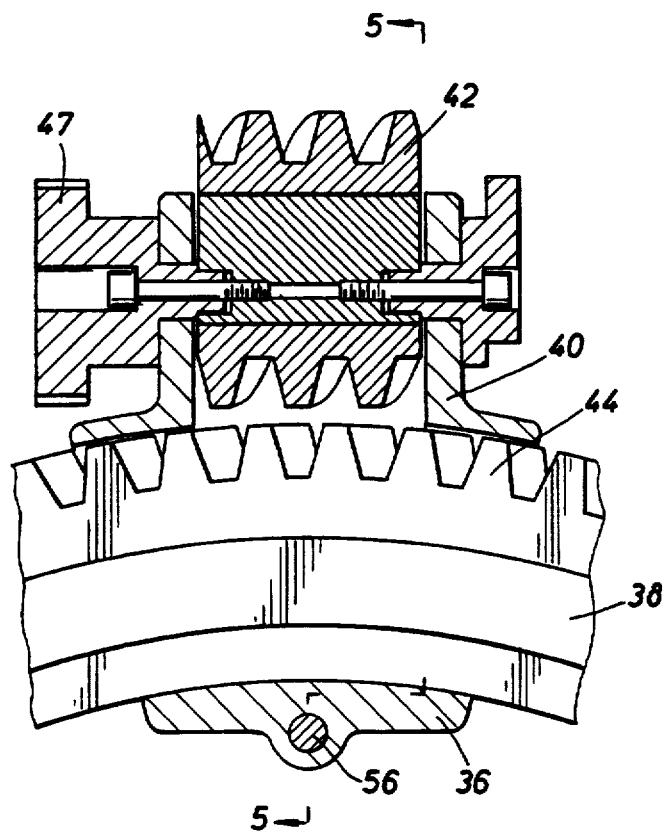
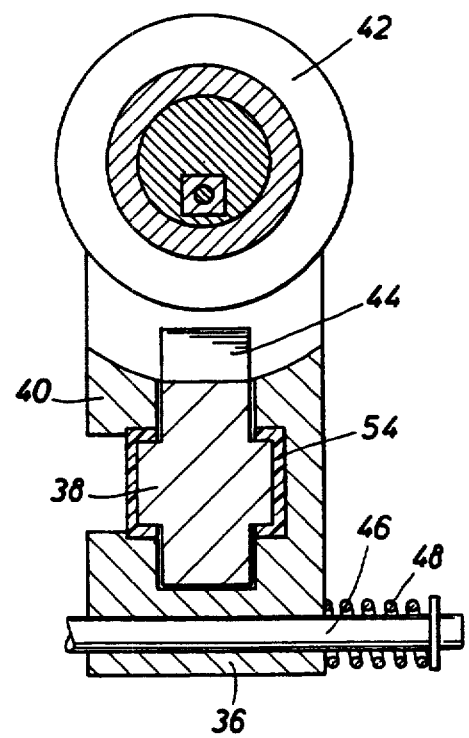
FIG. 6
FIG. 7
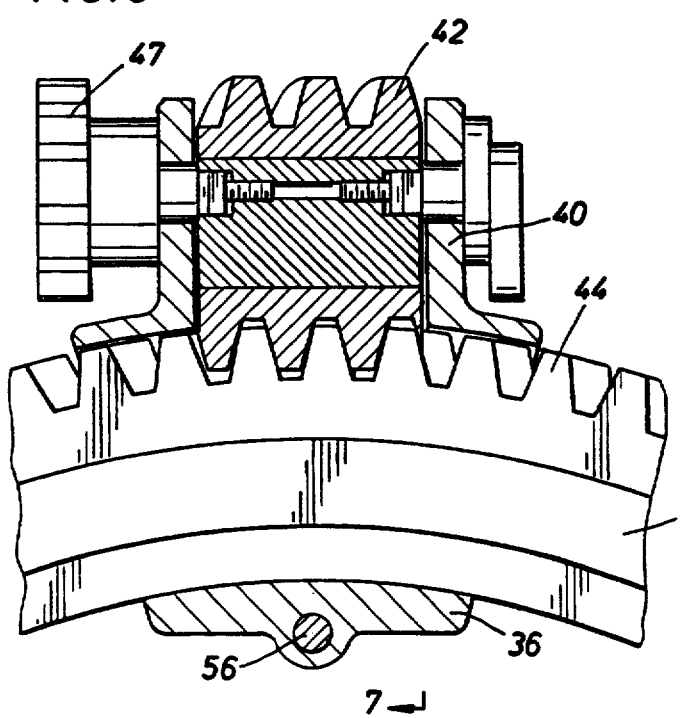
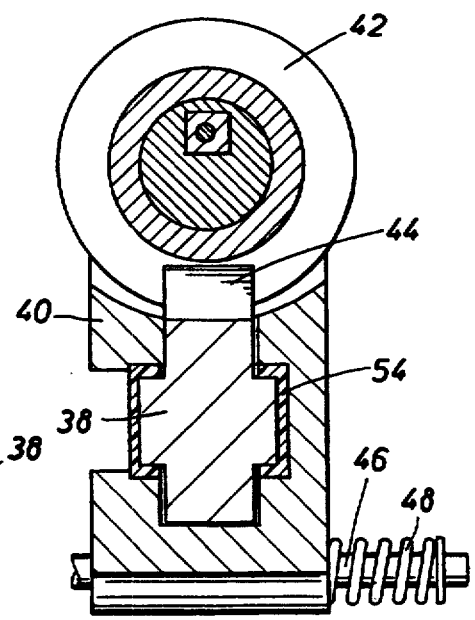

SUPINATION-PRONATION DEVICE

FIELD OF THE INVENTION

The present invention relates generally to the treatment of injuries and contractures of the elbow joint, particularly supination-pronation contracture and proximal radial head fractures, and more particularly to a device to prevent or correct supination-pronation contractures of the radial-ulnar joint.

BACKGROUND OF THE INVENTION

Contractures, a tendency for muscles, tendons or scar tissue to shorten in skeletal joints, are common after trauma and represent a major challenge in the care of such injuries. Routine and occupational tasks can be severely hindered by flexion-extension contractures of the humeral-ulnar joint as well as supination-pronation contractures of the proximal radial-ulnar joint which controls rotational motion of the radius about the axis of the ulna.

Current approaches to the treatment of elbow trauma have more aggressively sought to prevent contracture and stiffness through movement. Methods of rigid internal fixation with sufficient stability to allow motion within days after injury rather than closed treatment and immobilization in a cast have been developed. In the treatment of dislocations, protected early motion is now begun as soon as the patient is comfortably able to do so.

However, the currently available techniques for the prevention of contracture are not uniformly successful. Early active motion alone can reduce the severity of contracture, but requires the patient's own strength, compliance and constant effort. Passive stretching by a therapist can be done on a very limited basis and it is applied slowly, but such therapy risks the formation of heterotopic bone and myositis ossifications. Dynamic splints may be used, but these require pressure on the sometimes sensitive or injured soft tissues of the arm and forearm and thus may reduce patient compliance, or may not be possible to use, i.e., in burn injury.

Additionally, fractures of the proximal radius that require distraction have been treated in the past with simple pin fixation holding the ulna fixed to the radius. While fixed to the ulna, contracture and loss of motion occur.

Recently, a device was developed which permits aligned flexion and extension of the elbow during fixation to treat or prevent flexion-extension contracture at this joint. See U.S. Pat. No. 5,102,411. However, no known device is available to prevent or correct supination-pronation contracture at the elbow joint.

It would be highly desirable to provide a mechanical device for the prevention or correction of contracture of the proximal radial-ulnar joint controlling the motions of pronation and supination. It would be further desirable to provide a device which permits distraction of fractures of the radial-ulnar joint as well as motion to optimize control of the fracture and permit motion during healing, thereby reducing the tendency for contracture and loss of motion.

SUMMARY OF THE INVENTION

In order to solve the problems described above, a mechanical device to prevent or correct supination-pronation contracture of the elbow joint is provided which includes proximal and distal external bracing sections, respectively connected to the ulna and the radius of the forearm. The bracing sections are connected to the respective skeletal elements through support rings which encircle at least part of the forearm and are connected to integral bone through wires or pins.

The bracing sections are connected to each other for example by means of connecting rods which serve to stabilize the device. The distal bracing section includes a gear-toothed adjustment arc and a slidable carriage designed to engage and be retained about the arc. The slidable carriage is adapted to contain and permit continued adjustment of a distal pin, which pin connects the distal bracing section to the distal radius. The slidable carriage further includes a worm brace housing and an eccentrically mounted worm drive designed to selectively engage with the gear-teeth of the arc, permitting movement of the slidable carriage along the arc, and thereby causing movement of the radius through its attached distal pin.

The distal pin is connected to the device at the slidable carriage through an adjustment rod which allows continuous adaption of the device in at least three planes. In the exemplified embodiment, the first plane is approximately perpendicular to the axis of the ulna, along the axis of the pin, as the adjustment rod slides toward or away from the radius along the pin. The second direction is approximately parallel to the axis of the ulna as the adjustment rod slides within the slidable carriage altering the length of the adjustment rod between the distal pin and the slidable carriage. Rotation of the adjustment rod within the slidable carriage is permitted as well as rotational movement of the adjustment rod about the distal pin. The multiple degrees of movement permitted by the device allow for continued adaption of the device during pronation and supination motions in compensation for the conical path taken by the radius in its rotation about the ulna. In addition, the continued adaption also compensates for the uncertainty of locating the true axis of rotation of the radius about the ulna. Adjustment of the distance between the two bracing sections also permits slight distraction of the radius, desirable, for example, in the treatment of proximal radial head articular fractures.

The distal bracing section includes a gear mechanism which can be used for moving the slidable carriage along the toothed arc and consequently moving the attached radius relative to the ulna through the application of external force to the gear mechanism. The external force may be applied through a manually operated crank or a motor in order to stretch soft tissue surrounding the joint and thereby address joint contracture. A selective engagement mechanism is also provided so that the gear mechanism may be selectively engaged or disengaged. Disengagement allows the joint to move freely under the patient's own muscle force through pronation and supination.

By providing the mechanism as described, supination-pronation contractures of the elbow joint can be prevented through active or passive movement through the joint.

BRIEF DESCRIPTION OF THE DRAWINGS

A better understanding of the invention can be attained from the detailed description of a preferred embodiment set forth below, when considered in conjunction with the appended drawings, in which:

FIG. 4 is a perspective view of the distal bracing section, partially in section showing the disengaged gear mechanism;

FIG. 5 is a sectional view of the disengaged gear mechanism;

FIG. 6 is a perspective view of the distal bracing section partially in section showing the engaged gear mechanism;

FIG. 7 is a sectional view of the engaged gear mechanism;

DETAILED DESCRIPTION OF THE INVENTION

Figure 1:
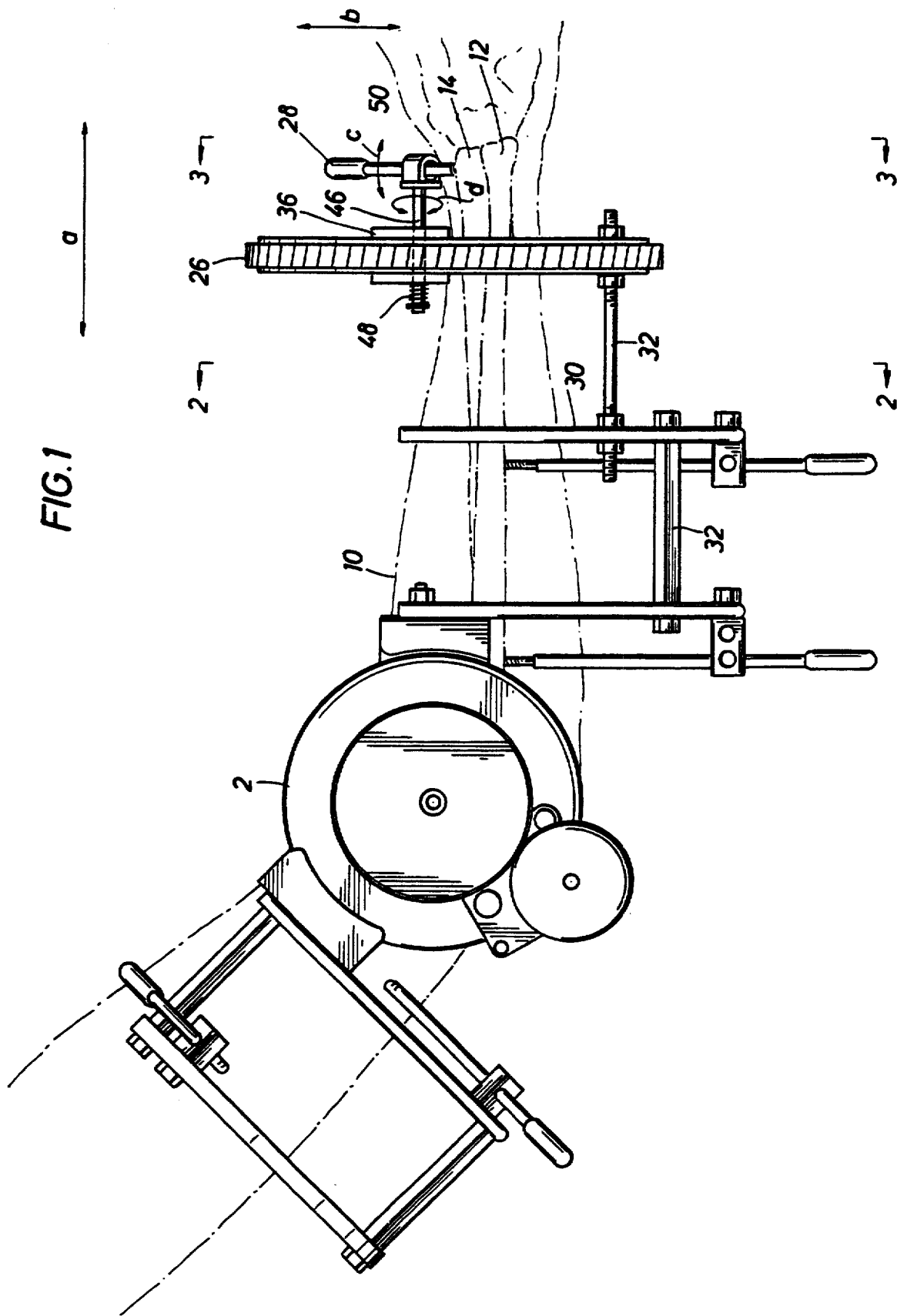
FIG. 1 is a side plan view of the supination-pronation device which is the subject of the present invention, as the device would be connected to the forearm of a patient.

The supination-pronation device in a preferred embodiment of the present invention is shown as it would be connected to the forearm of a patient in FIG. 1, where reference numeral 10 identifies dashed lines illustrating the forearm of a patient. Dashed lines 12 represent the ulna and dashed lines 14 the radius bones of the forearm. The device includes a proximal bracing section 16 and a distal bracing section 26.

Each bracing section 16, 26 is attached to its appropriate skeletal element 12, 14 by means of pins 18, 28, e.g., percutaneous pins. At least one proximal pin 18 fixes the proximal bracing section 16 to the ulna 12 and at least one distal pin 28 attaches the distal bracing section 26 to the radius 14. It is preferred that the pin(s) fixing the device to the ulna be placed in the medial aspect, e.g. subcutaneous border of the mid to proximal portion of the ulna and that the pin(s) attaching the device to the radius be placed in the lateral aspect of the distal radius.

It is understood that the device may utilize a placement other than that exemplified in the drawings, i.e., a reverse placement such that rotation of the device is proximal and fixation of the device is proximal on the forearm. The preferred placement is that which will assist and not interfere with therapeutic stabilization of the skeletal elements and joints and that which will allow full range of supination-pronation movements. When the device is to be used independently, i.e., not in concert with the dynamic elbow support, more than one proximal pin may be required to stably fix the device at the ulna. Multiple pins may be placed in the ulna, preferably in the mid to proximal portion and in the medial or posterior aspect to avoid interference with supination-pronation movements.

Preferably, the distance between the proximal and distal bracing sections may be adjusted to permit slight distraction of the radius e.g. as needed in the treatment of proximal radial head articular fractures.

Figure 2:
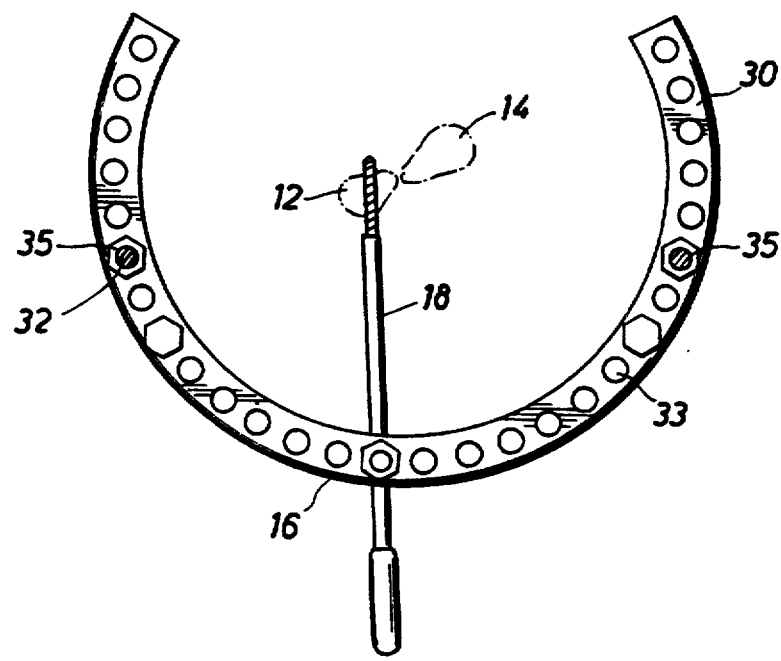
FIG. 2 is a partial plan view of the proximal bracing section, for fixing the device to the mid to proximal ulna.

Referring now to FIG. 2, the proximal bracing section 16 includes one or more annular support rings 30 which may be formed in a closed or partial circle, and contain a plurality of openings 33 around their circumference. The support rings 30 can be similar to ones developed by Dr. Ilizarov for use in bone lengthening or rehabilitation techniques which are commonly known as Ilizarov rings. In a preferred embodiment, the proximal bracing section 16 of the supination-pronation device of the present invention is the distal bracing section of a dynamic elbow hinge 2 such as is disclosed in U.S. Pat. No. 5,102,411.

Figure 3:
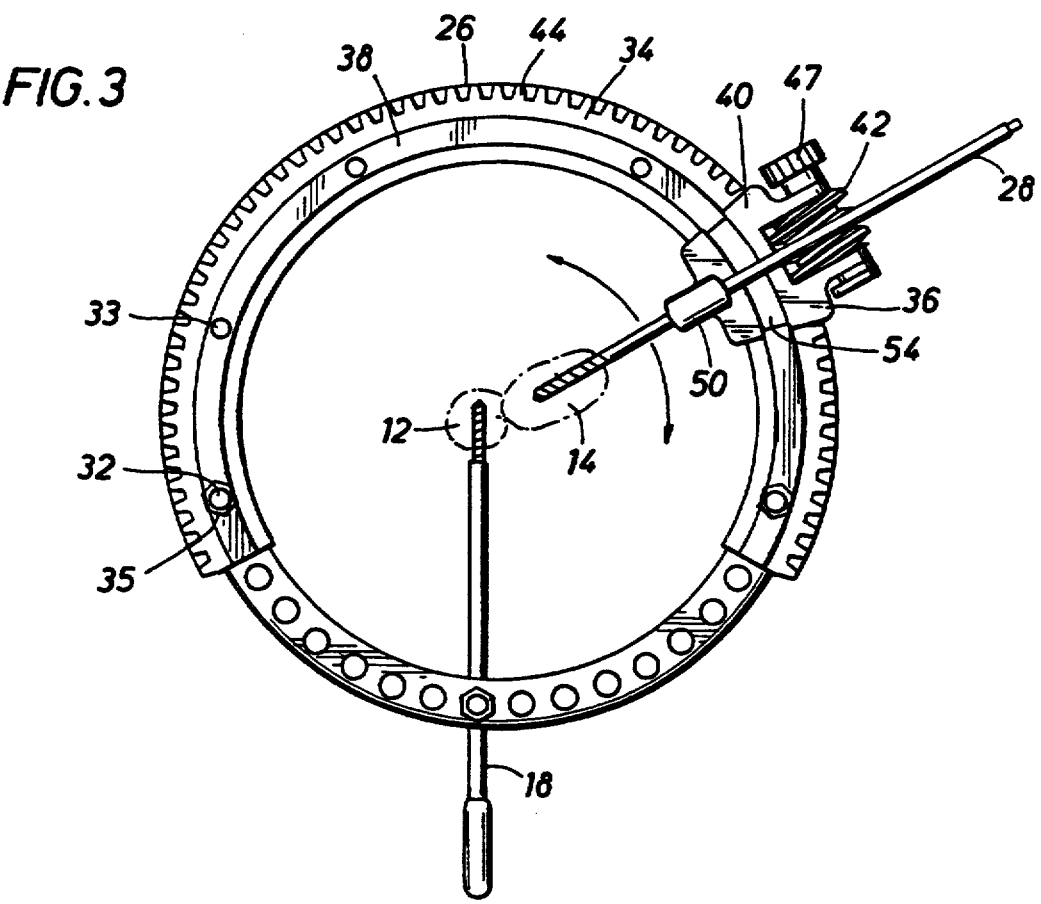
FIG. 3 is an end, plan view of the device.

Rods 32 extend between the annular support rings 30 when more than one is used, and rods 32 also extend between the annular support rings 30 of the proximal bracing section 16 and the distal bracing section 26. In the exemplified embodiment shown in FIGS. 1-3, threaded rods 32 pass through openings 33 in the annular support rings 30 and in the arc 34, and are locked by nuts 35, to secure the proximal and distal bracing sections to each other at a desired distance. Adjustment of the axis of the device in a direction approximately parallel to the axis of the ulna 12 is thus achieved by altering the distance between the proximal and distal bracing sections 16, 26 by changing their relative positions on rods 32. Slight distraction of the radius may also be achieved by adjusting this distance.

The distal bracing section 26 includes a movement means for moving the radius 14 about the ulna 12. In the exemplified embodiment shown in FIG. 3, the movement means includes an adjustment arc 34 and a slidable carriage 36. The slidable carriage 36 is adapted to mate with a track 38 in the arc 34, and engage and be retained thereabout. The slidable carriage 36 is also adapted to engage and slide along the track 38, and preferably includes bearings 54 for reduced friction.

The slidable carriage includes a worm brace or worm housing 40 and a worm drive 42. The worm drive mates with gear teeth 44 of the arc 34 such that rotation of the worm drive 42 causes movement of the slidable carriage 36 along the track 38 of the arc 34. Such movement of the slidable carriage 36 and its attached distal pin 28 along the arc 34 of the distal bracing section 26 causes rotation of the attached radius 14 about the ulna 12.

A selective engagement mechanism is provided to selectively disengage the worm drive 42 with the gear teeth 44 of the arc 34 so that the patient may use his or her own power to move the joint through supination and pronation. The selective engagement mechanism may be, for example as shown in FIGS. 4-7, an eccentrically mounted worm drive 42 which is selectively disengaged (FIGS. 4 and 5) or engaged (FIGS. 6 and 7) with the gear teeth 44 of the arc 34 by turning a thumbwheel 47. When the worm drive 42 is engaged, as shown in FIGS. 6 and 7, movement of the slidable carriage 36 along the track 38 of the arc 34 is achieved by turning of the worm drive 42. When the worm drive 42 is disengaged, as shown in FIGS. 4 and 5, the teeth 44 of the arc 34 are disengaged from contact with the worm drive 42, permitting free movement of the slidable carriage 36 along the track 38 of the arc 34.

Figure 8:
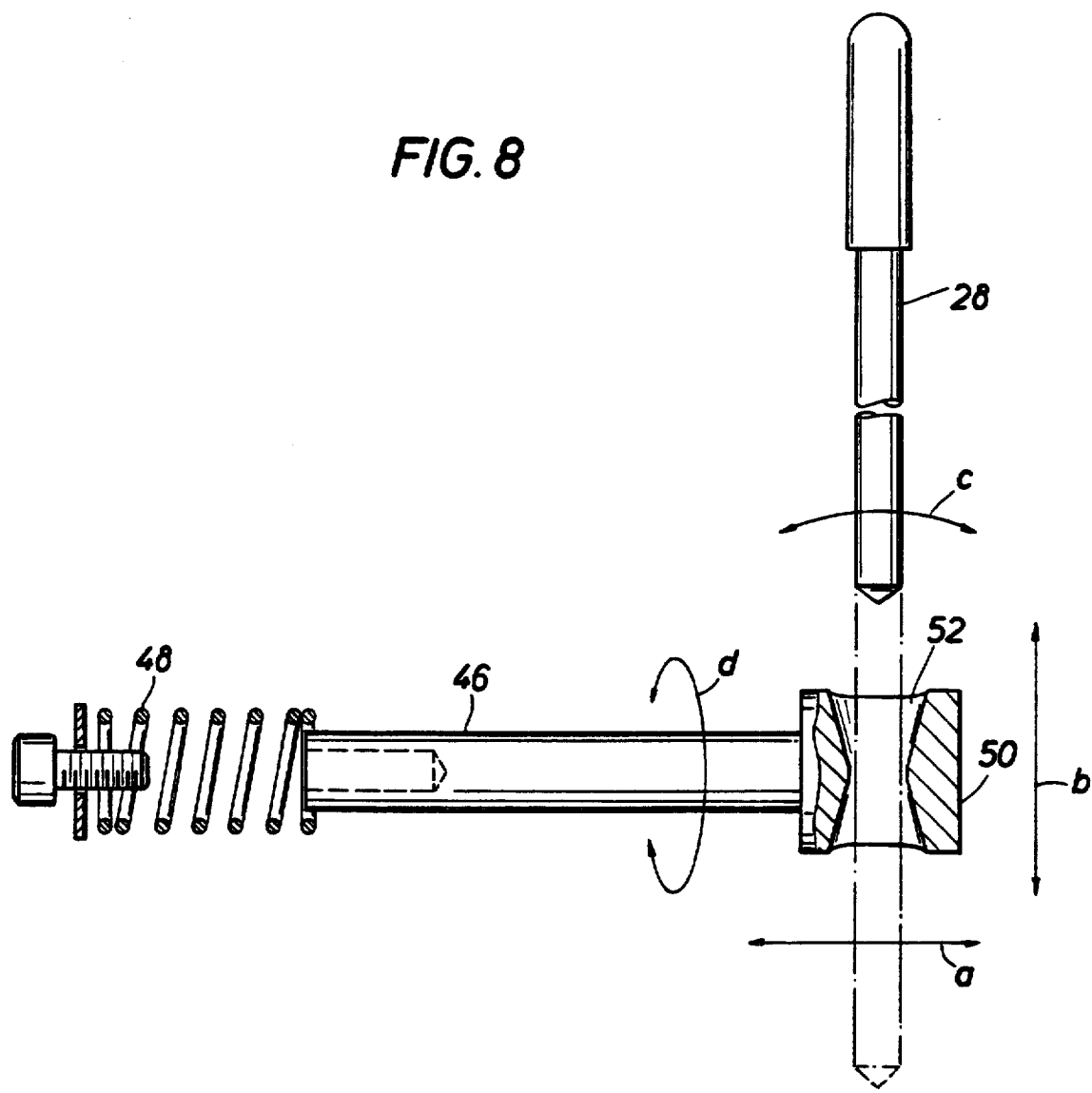
FIG. 8 is a plan view partially in section of an adaption mechanism with arrows showing possible directions of adjustment.
Figure 9:
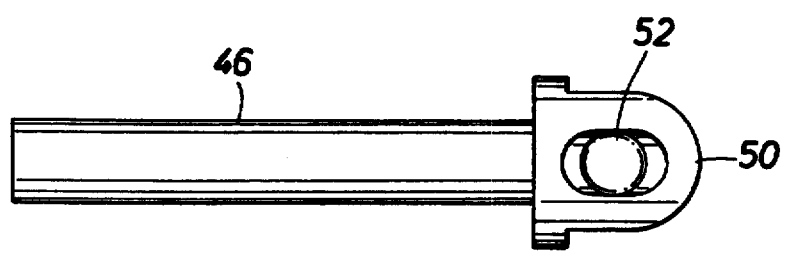
FIG. 9 is a top plan view of an adjustment mechanism.

As shown in FIG. 1 the distal pin 28 is connected to the slidable carriage 36 through an adjustment rod 46 movably mounted in the slidable carriage 36. The slidable carriage 36 is adapted to receive and movably contain the adjustment rod 46, for example, as shown in FIGS. 4 and 6 through an opening 56 in the slidable carriage 36. Within the opening 56 of the slidable carriage 36, the adjustment rod 46 is permitted to rotate and move axially as shown by arrow a in FIGS. 1 and 8. A spring 48 biases the adjustment rod 46 away from the distal pin 28. The adjustment rod 46 includes an adjustment sleeve 50 which is adapted to receive and movably engage the distal pin 28, for example as shown in FIGS. 8 and 9, through an opening 52 in the adjustment sleeve 50. Preferably, the opening 52 in the adjustment sleeve 50 includes a semiconical relief area to permit pivotal motion of the adjustment sleeve 50 about the distal pin 28. The adjustment means thus described permits rotation of the adjustment rod 46 within the slidable carriage 36, movement of the adjustment rod 42 within the slidable carriage 36 in a direction approximately parallel to the axis of the ulna 12, movement of the adjustment sleeve 50 along the distal pin 28 approximately perpendicular to the axis of the ulna 12, and pivotal movement of the adjustment sleeve 50 about the distal pin 28.

Referring to FIG. 1, the supination-pronation device of the present invention may be preassembled by connecting all parts with the exception of the pins. The device may be installed by placing fixation pins in the ulna 12, preferably in the medial, subcutaneous border of the mid to proximal portion of the ulna 12 and attaching the preassembled device thereto. The device may be adjusted by altering the distance between bracing sections using the threaded connecting rods 32. Preferably with a load on the spring 48, the distal pin 28 is inserted through the adjustment sleeve 50 and fixed to the distal radius 14, preferably in the lateral aspect of the distal radius while the forearm is in pronation.

Through the mechanism described, the device permits supported and continually adapting or adjusting movement of the radius about the ulna for protected motions of supination and pronation. Once the device is installed, a patient can have his or her forearm moved in supination and pronation motions through the application of force to the gearing mechanism. Once maximum movement is achieved for the patient, the engaged worm resists the soft tissues, resulting in a progressive stretching of the soft tissues to permit greater ranges of motion. The selective engagement mechanism may be employed to disengage the worm drive so that the patient can actively move his or her forearm through supination and pronation movements. If actively moving, the worm may be engaged to lock the position, e.g. of greatest motion achieved to begin stretching the soft tissues. In this way, the patient progressively increases the range of motion by stretching the soft tissues and locking the device in place. As treatment progresses, greater ranges of motion are achieved.

The supination-pronation device of the present invention is useful in the treatment of trauma to the arm and forearm such as severe fractures, dislocations of the elbow and the like as well as other trauma where a high possibility of stiffness or contracture at the proximal radial-ulnar joint normally results from immobilization. The device may be applied immediately to the patient to begin rehabilitation and to prevent contracture. In a preferred embodiment, the device may be attached to the dynamic elbow hinge described in U.S. Pat. No. 5,102,411 and used in conjunction with that device.

The supination-pronation device permits support and protected movement through supination and pronation as needed during joint therapy without significant interference with the joint using external adjustment mechanisms.

The device of the present invention may be fabricated using materials known in the field. It is preferred that the materials used to fabricate the device permit sterilization of the device. Also preferred are materials which are radiotranslucent to permit monitored therapy of the injury through X-ray imaging without interference from the device.

The foregoing description is considered to be illustrative and not limiting. Variations and improvements of the invention can be made without departing from the spirit and scope of the invention. All such variations and improvements are contemplated as falling within the scope of the appended claims, which:

We claim:

1. A device for the treatment of supination-pronation contracture at a patient's radial-ulnar joint comprising:
   first and second bracing sections;
   rigid connecting means for rigidly connecting the first and second bracing sections to each other;
   first connecting means for rigidly connecting the first bracing section to the radius;
   second connecting means for connecting the second bracing section to the ulna; and
   movement means operatively connected to the first connecting means for rotating the first connecting means and consequently the radius about the ulna.

2. The device of claim 1 further comprising adjustment means for providing continuous adjustment of the position and orientation of the first connecting means with respect to the first bracing section as the radius is rotated about the ulna.

3. The device of claim 1 wherein the movement means includes a gear means for mating with said first bracing section and for moving the movement means and consequently the connected radius relative to the first bracing section and consequently about the ulna in supination and pronation in response to external force applied to the gear means.

4. The device of claim 3 wherein said gear means further comprises a selective engagement means for selectively engaging said gear with said first bracing section such that force is transferred between the gear and the first bracing section to restrict free motion of the skeletal elements and permit controlled movement in supination and pronation and for selectively disengaging the gear and the first bracing section to allow the skeletal elements to move freely.

5. The device of claim 1 wherein said first bracing section includes a threaded pin adapted to engage bone.

6. The device of claim 5 further including an adjustment rod connecting the pin with the first bracing section, the rod including a sleeve for slidably engaging the pin.

7. The device of claim 6 further including means for connecting the adjustment rod to the first bracing section, said means allowing the rod to simultaneously move axially and rotationally relative to the first bracing section.

8. The device of claim 7 further including a spring means for biasing the rod away from the pin.

9. The device of claim 6 wherein said sleeve includes an opening having a semiconical relief area permitting pivotal movement of the pin within the sleeve.

10. The device of claim 1 further comprising:
    distraction means for adjusting the distance between the first and second bracing sections thereby causing distraction of the radius.

11. A device for the treatment of supination-pronation contracture at a patient's radial-ulnar joint comprising:

proximal and distal bracing sections; rigid connecting means for rigidly connecting the proximal and distal bracing sections to each other;

proximal connecting means for rigidly connecting the proximal bracing section to the ulna;

distal connecting means for connecting the distal bracing section to the radius; and movement means operatively connected to the distal connecting means for rotating the distal connecting means and consequently the radius about the ulna.

12. The device of claim 11 further comprising:
distraction means for adjusting the distance between the proximal and distal bracing sections thereby causing distraction of the radius.

13. The device of claim 11 further comprising:
dynamic elbow hinge operatively connected to the proximal bracing section.

* * * * *